United States Patent [19]

Seghi

[11] Patent Number: 5,062,832

[45] Date of Patent: Nov. 5, 1991

[54] ANTICONTAGION DEVICE FOR INJECTING DENTAL ANESTHETIC SOLUTIONS CONTAINED IN CARTRIDGES

[75] Inventor: Giovanni Seghi, Firenze, Italy

[73] Assignee: L. Molteni & C. dei F.lli Alitti S.p.A., Scandicci, Italy

[21] Appl. No.: 432,859

[22] Filed: Nov. 7, 1989

[51] Int. Cl.⁵ ............................................. A61M 5/00
[52] U.S. Cl. .................................. 604/110; 604/218; 433/89
[58] Field of Search ........................... 433/80, 89, 90; 222/147, 327, 391; 604/110, 228, 232

[56] References Cited

U.S. PATENT DOCUMENTS 3,478,937 11/1969 Solowey ............................... 604/110
4,838,863 6/1989 Allard et al. ......................... 604/110

FOREIGN PATENT DOCUMENTS 8900432 1/1989 France ................................. 604/110
2205750 12/1988 United Kingdom ................. 604/110

Primary Examiner—Stephen C. Pellegrino
Assistant Examiner—Michael Rafa
Attorney, Agent, or Firm—Birch, Stewart, Kolasch & Birch

[57] ABSTRACT

An anticontagion device for injecting dental anesthetic solution contained in cartridges, comprising a cartridge-holding sleeve for once-only use, which is closed by a non-removable plug and fitted to a piston mechanism.

7 Claims, 3 Drawing Sheets

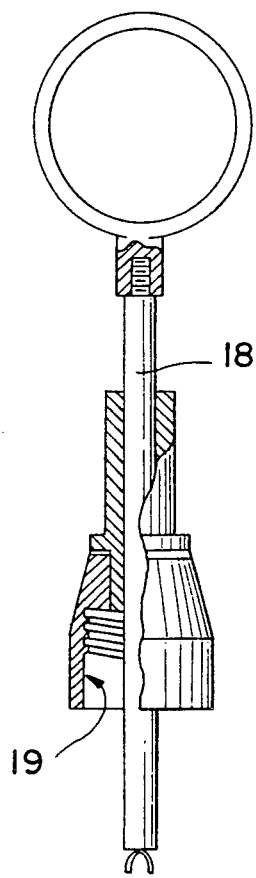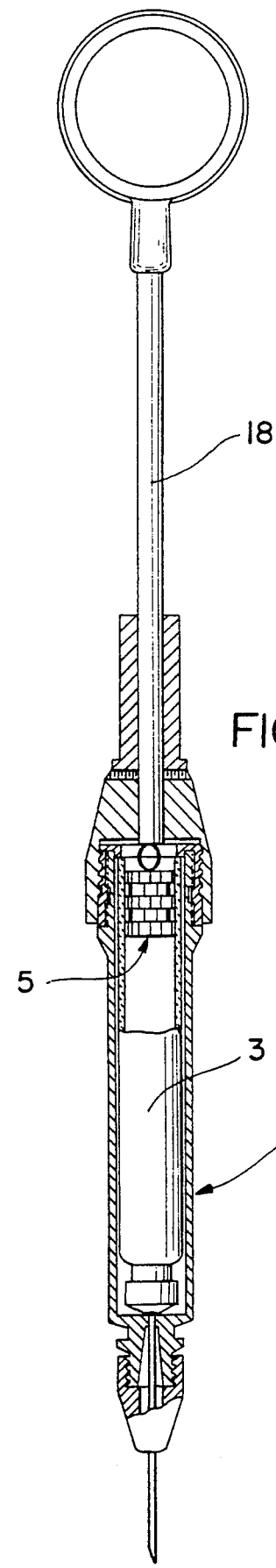
FIG. 8
FIG. 9

ANTICONTAGION DEVICE FOR INJECTING DENTAL ANESTHETIC SOLUTIONS CONTAINED IN CARTRIDGES

PRIOR ART

In dentistry, essentially two types of local anesthesia devices are known.

One type of device is in the form of a pistol comprising a piston mechanism for pushing the plunger of the cartridge containing the anesthetic liquid, and a cartridge-holding sleeve of steel construction which is fitted to the pistol by screwing. A double-point needle is applied to the free end of the cartridge-holding sleeve.

Another type of known device comprises a piston mechanism carrying a fixed body containing a housing into which the cartridge is inserted, the double-point needle being applied to the end of this body.

From the operational viewpoint said devices are suitable for their purpose, however they have the serious drawback of possibly being a carrier of infection. In this respect, the cartridge holding sleeve and the cartridge housing of the two devices can transmit infective germs from one patient to the next if insufficiently sterilized.

SUMMARY OF THE INVENTION

The aim of the present invention is therefore to provide a new device for injecting dental anesthetic solutions contained in cartridges which has the advantage of excluding any possibility of contagion, in that the cartridge-holding sleeve is used once only.

Said device comprises a piston mechanism for pushing the cartridge plunger, a cartridge-holding sleeve and a plug for closing said sleeve, and is characterised in that said sleeve and said plug are provided with means such that when fitted one on the other they cannot be separated, said plug and said piston mechanism being provided with an external and an internal thread respectively to enable the plug-sleeve-cartridge assembly to be fitted to said piston mechanism.

DESCRIPTION OF THE INVENTION

The characteristics and advantages of the device according to the present invention will be more apparent from the detailed description given hereinafter with reference to the figures which show preferred embodiments of the invention by way of non-limiting example only.

FIG. 8 shows the piston mechanism; and

FIG. 9 shows the connection between the piston mechanism and the plug-sleeve-cartridge assembly.

Figure 1:
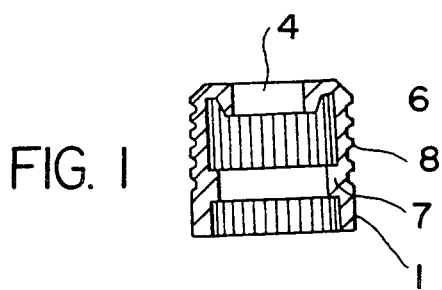
FIG. 1 shows the plug for the cartridge-holding sleeve.
Figure 2:
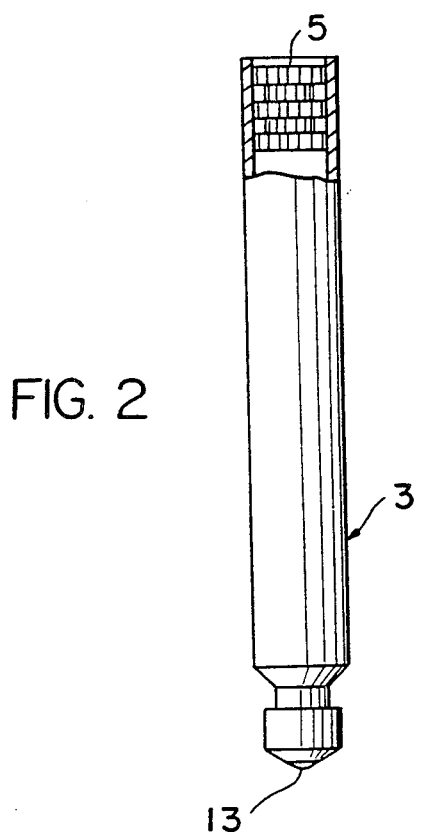
FIG. 2 shows the cartridge containing the anesthetic liquid.
Figure 3:
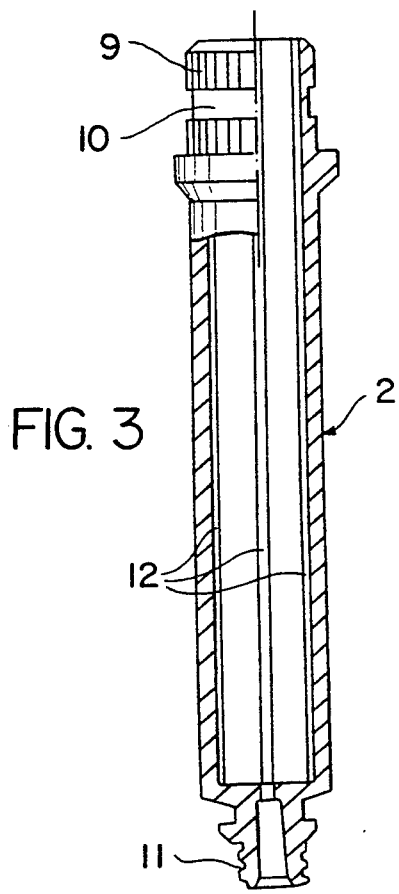
FIG. 3 shows the cartridge-holding sleeve.

Using the reference numerals and letters of FIGS. 1, 2, 3, 6, 7, 8 and 9 the plug, the cartridge-holding sleeve and the cartridge are indicated overall by 1, 2 and 3 respectively.

The plug 1 comprises inner vertical knurling 6, an inwardly projecting step 7, an external thread 8, and an axial bore 4 for passage of the piston, the purpose of which is to push the plunger 5 of the cartridge 3 (FIGS. 8 and 9).

The cartridge-holding sleeve 2 comprises at its top end a vertical knurling 9 and a recess 10, and at its opposite end a thread 11 for fitting the double-point needle, and in its inner surface four notches 12 for fixing the cartridge 3.

The cartridge 3 is of the commonly used type and is provided with a plunger 5 designed to be pushed by the piston mechanism, and a rubber seal 13 through which one point of the double-point needle in inserted.

Figure 6:
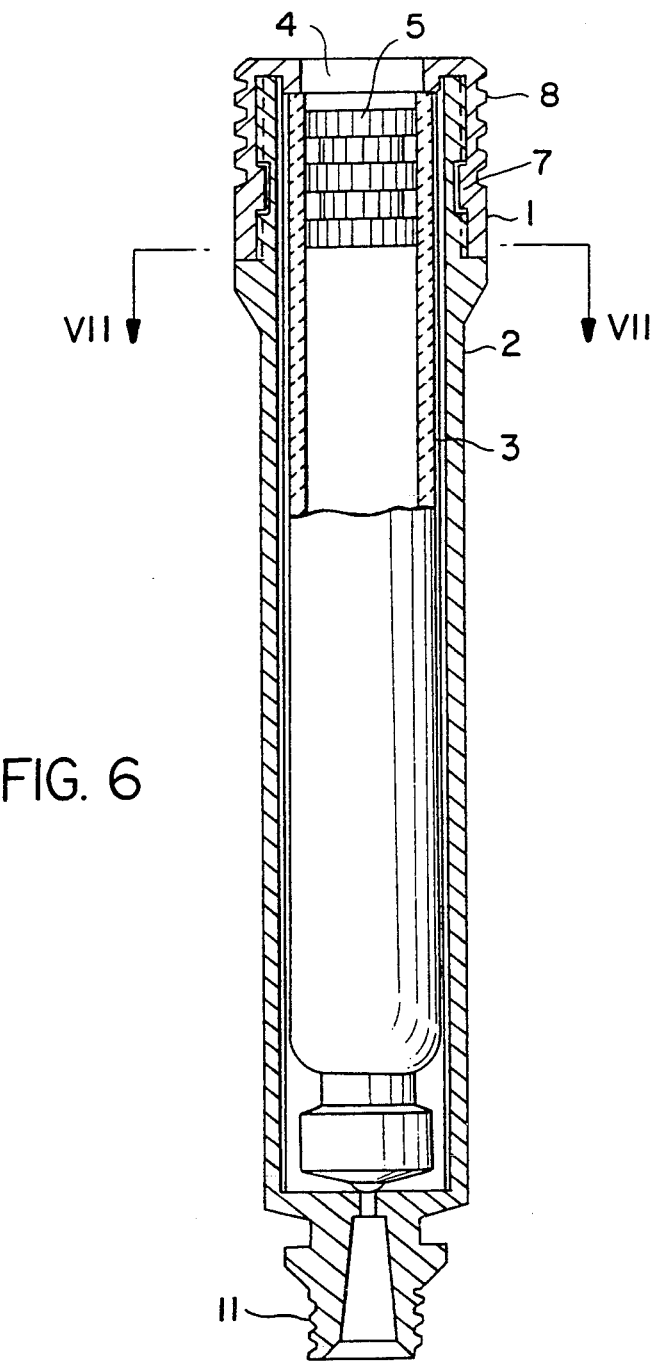
FIG. 6 is a longitudinal section through the assembly comprising the cartridge-holding sleeve, plug and cartridge ready for fitting to a piston mechanism.
Figure 7:
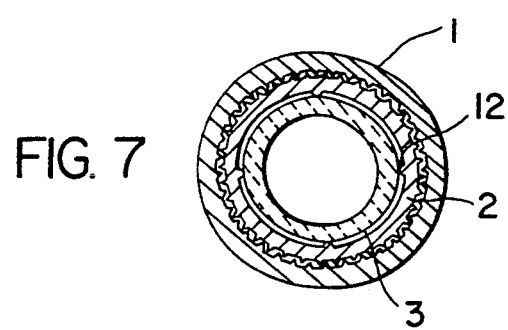
FIG. 7 is a cross-section through said assembly.

The assembly of the described elements is shown in FIGS. 6 and 7, this latter representing a cross-section on the line VII—VII of FIG. 6.

When the cartridge 3 has been inserted into the sleeve 2, the plug 1 is applied to the top end of the sleeve 2. The application is done by forcing so that the step 7 snap-fits into the recess 10.

At this point the sleeve-cartridge-plug assembly is screwed by its thread, 8 into the corresponding thread 19 provided in the piston mechanism FIGS. 8 and 9).

From the figures it is apparent that when the plug 1 has been applied to the sleeve 2, the fact that the step 7 has fitted into the recess 10 prevents any separation of the plug, so that when the anesthetic has been used the sleeve-plug-cartridge assembly must necessarily be thrown away.

Figure 4:
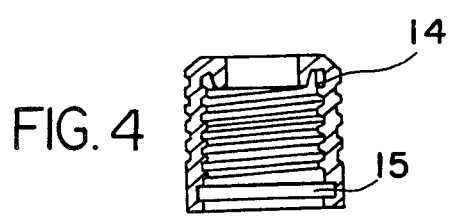
FIGS. 4 and 5 show a further embodiment of the plug and cartridge-holding sleeve.
Figure 5:
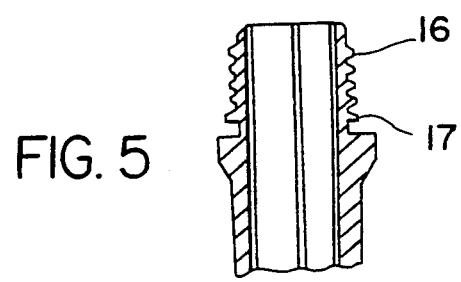

A. further method of locking the plug to the cartridge-holding sleeve is shown in FIGS. 4 and 5.

In this embodiment the plug comprises an internal thread 14 and an internal recess 15, whereas the top end of the sleeve comprises an external thread 16 and a projecting tooth 17. On screwing the plug into the top end of the sleeve, the tooth 17 engages in the recess 15 to make any separation of the plug impossible. Thus also in this case the sleeve-plug-cartridge assembly has to be thrown away after being used only once.

The plug and sleeve are constructed of transparent thermoplastic material.

From the aforegoing description and figures it is apparent that the invention attains the proposed object in that because the plug is locked onto the sleeve, this part of the device, which can be an infection carrier, has to be thrown away after being used only once, so preventing any possibility of infection.

I claim:

1. An anticontagion device for injecting dental anesthetic solutions, which comprises a cartridge containing anesthetic solution and having a plunger, received therein a piston mechanism for pushing the plunger of the cartridge, a cartridge holding sleeve adapted to receive said cartridge therein and a plug for closing the upper end of said sleeve, means being provided between said sleeve and said plug such that when they are fitted one on the other they cannot be separated, said plug and said piston mechanism being provided respectively with an external and an internal thread to enable the plug-sleeve-cartridge assembly to be fitted to said piston mechanism, by engagement of said threads.

2. The device as claimed in claim 1, wherein said plug comprises inner vertical knurling, an inwardly projecting step, and an external thread.

3. The device as claimed in claim 1, wherein said sleeve comprises, at its top end, vertical knurling and a recess.

4. The device as claimed in claim 1, wherein said means which prevent the plug separating from the sleeve consists of a projecting step and a recess, which are engaged by a snap fit.

5. The device as claimed in claim 1, wherein said plug comprises an internal thread and an internal recess.

6. The device as claimed in claim 1, wherein said sleeve comprises at its top end an external thread and a projecting tooth.

7. The device as claimed in claim 1, wherein said means which prevents the plug separating from the sleeve consists of a recess and a projecting tooth, which engage with one another.

* * * * *